United States Patent
Korenev et al.

(10) Patent No.: US 9,234,444 B2
(45) Date of Patent: Jan. 12, 2016

(54) FLAME DETECTION SYSTEM FOR PARTICULATE FILTER REGENERATION

(71) Applicant: CATERPILLAR INC., Peoria, IL (US)

(72) Inventors: Sergey Korenev, College Station, TX (US); William Love, Dunlap, IL (US); Kevin Dea, Morton, IL (US); Jason Bloms, Edwards, IL (US); Timothy Feucht, Edelstein, IL (US); Richard Holland, Shropshire (GB)

(73) Assignee: Caterpillar Inc., Peoria, IL (US)

( * ) Notice: Subject to any disclaimer, the term of this patent is extended or adjusted under 35 U.S.C. 154(b) by 69 days.

(21) Appl. No.: 13/781,486

(22) Filed: Feb. 28, 2013

(65) Prior Publication Data
US 2014/0238233 A1    Aug. 28, 2014

(51) Int. Cl.
| | |
|---|---|
| *B01D 46/46* | (2006.01) |
| *F01N 3/025* | (2006.01) |
| *F01N 3/38* | (2006.01) |
| *F01N 11/00* | (2006.01) |
| *F01N 9/00* | (2006.01) |
| *G01N 27/62* | (2006.01) |

(52) U.S. Cl.
CPC *F01N 3/025* (2013.01); *F01N 3/38* (2013.01); *F01N 11/00* (2013.01); *F01N 9/002* (2013.01); *F01N 2550/04* (2013.01); *F01N 2560/12* (2013.01); *G01N 27/626* (2013.01); *Y02T 10/47* (2013.01)

(58) Field of Classification Search
CPC ... F01N 3/025; F01N 13/008; F01N 2240/14; F01N 2240/28; F01N 2240/30; Y02T 10/47; B01D 46/0086; B01D 53/0454; B01D 2259/402

See application file for complete search history.

(56) References Cited

U.S. PATENT DOCUMENTS

| | | | | |
|---|---|---|---|---|
| 3,836,316 | A | * | 9/1974 | Ikegami et al. .................. 431/79 |
| 4,963,857 | A | * | 10/1990 | Sackett ......................... 340/606 |
| 5,049,063 | A | * | 9/1991 | Kishida et al. ................... 431/78 |
| 7,171,801 | B2 | | 2/2007 | Verkiel et al. |
| 7,240,483 | B2 | | 7/2007 | Cizeron et al. |

(Continued)

OTHER PUBLICATIONS

Sadami Yoshiyama et al., Fundamental Study on Combustion Diagnostics Using a Spark Plug as Ion Probe, International Fall Fuels and Lubricants Meeting and Exposition, Baltimore, MD, Oct. 16-19, 2000.

(Continued)

*Primary Examiner* — Amber Orlando
(74) *Attorney, Agent, or Firm* — Finnegan, Henderson, Farabow, Garrett & Dunner, LLP (57) ABSTRACT

A flame detection system is disclosed. The system may have a flame chamber and a filter, wherein the filter includes filter media configured to collect matter from an engine exhaust. Additionally, the filter may be disposed downstream of the flame chamber. An ignition device may be disposed in the flame chamber and may be configured to ignite a flame in the flame chamber to regenerate the filter. A sensor may be disposed proximate the ignition device, and may be configured to sense a change in electrical conductivity that is indicative of a presence of the flame in the flame chamber.

8 Claims, 4 Drawing Sheets

(56) References Cited

U.S. PATENT DOCUMENTS

| | | | |
|---|---|---|---|
| 7,406,822 B2 | 8/2008 | Funke et al. | |
| 2007/0079817 A1* | 4/2007 | VanDyne et al. | 123/568.21 |
| 2009/0241520 A1* | 10/2009 | Gendron et al. | 60/295 |
| 2011/0283685 A1* | 11/2011 | Kotrba et al. | 60/286 |
| 2011/0289906 A1* | 12/2011 | Morley et al. | 60/320 |
| 2013/0047590 A1* | 2/2013 | Charles et al. | 60/311 |
| 2014/0237999 A1* | 8/2014 | Olivier | 60/303 |

OTHER PUBLICATIONS

Sadami Yoshiyama et al., Combustion Diagnostics of a Spark Ignition Engine Using a Spark Plug as an Ion Probe, Powertrain & Fluid Systems Conference & Exhibition, San Diego, CA, Oct. 21-24, 2002.

Clark Paterson et al., Development of a Diesel Particulate Filter Burner Control System for Active Trap Regeneration, 2007 World Congress, Detroit, MI, Apr. 16-19, 2007.

\* cited by examiner

| I | II | III |
|---|---|---|
| RESISTIVITY OF FLAME PLASMA (KOhm) | VOLTAGE ON $R_O$ WITH FLAME (Volt) | VOLTAGE ON $R_O$ WITHOUT FLAME (Volt) |
| 10 | 12 | 1.2 |
| 20 | 7.2 | 1.2 |
| 30 | 5.2 | 1.2 |
| 40 | 4.13 | 1.2 |
| 50 | 3.6 | 1.2 |
| 60 | 3.2 | 1.2 |
| 70 | 2.9 | 1.2 |
| 80 | 2.72 | 1.2 |
| 90 | 2.55 | 1.2 |
| 100 | 2.4 | 1.2 |

FIG. 3

FIG. 4

FLAME DETECTION SYSTEM FOR PARTICULATE FILTER REGENERATION

TECHNICAL FIELD

The present disclosure is directed to a flame detection system, and more particularly, to a flame detection system for particulate filter regeneration.

BACKGROUND

Emissions from a diesel engine, gasoline engine, natural gas engine, and other engines known in the art, may include particulate matter and other pollutants carried with engine exhaust. Exhaust aftertreatment systems generally include a diesel particulate filter, a diesel oxidation catalyst, and a selective catalytic reduction catalyst placed in the engine exhaust to reduce the amount of pollutants released into the atmosphere. The exhaust aftertreatment systems may separate or convert the pollutants to less noxious compounds.

A diesel particulate filter may collect particulate matter and remove it from the exhaust. However, over time, particulate matter may build-up and clog the filter, thereby impairing filter performance. Filter regeneration methods are designed to remove the built-up particulate matter from the filter, and improve filtration capacity/characteristics of the filter. An active regeneration method includes burning the accumulated particulate matter at elevated temperatures to thereby increase the filtration capacity of the filter. During the regeneration process, a fuel and air mixture is typically injected into a flame chamber upstream of the filter. The mixture is then ignited with a flame to burn the particulate matter captured by the downstream filter.

U.S. Pat. No. 7,406,822 issued to Funke et al. on Aug. 5, 2008 (the '822 patent), describes an exemplary system and method for active filter regeneration. In particular, a flame sensing system of the '822 patent uses thermocouples to detect whether a flame is present upstream of a particulate filter, and to monitor the amount of fuel required to maintain a sufficient flame. When no flame is present, the system may terminate the injection of fuel. However, when a flame is present, the amount of fuel may be adequate and the system may monitor the presence of fuel.

While the system disclosed in the '882 patent may be capable of detecting the presence of a flame, such systems are typically plagued with several disadvantages. For example, although thermocouples may be configured to detect the presence of a flame, thermocouples typically have a slower response time than other sensors. As a result, systems injecting fuel based on signals received from such thermocouples may continue to inadvertently inject fuel into the flame chamber while a flame is no longer present. Such excess fuel may flow downstream into the filter, and may crack or melt the filter causing permanent damage to the filter. Additionally, thermocouple sensors may be required to be located directly in the flame. The extreme temperatures of the flame may decay the thermocouple so that it may no longer work properly.

The disclosed system is directed to overcoming one or more of the problems set forth above and/or other problems of the prior art.

SUMMARY

The present disclosure is directed to a flame detection system including a flame chamber, a filter, an ignition device, and a sensor. The filter may include filter media configured to collect matter from an engine exhaust, and may be disposed downstream of the flame chamber. The ignition device may be disposed in the flame chamber and configured to ignite a flame in the flame chamber to regenerate the filter. The sensor may be disposed proximate the ignition device, and may be configured to sense a change in electrical conductivity that is indicative of a presence of the flame in the flame chamber.

The present disclosure is directed to a method of determining the presence of a flame within a flame chamber of a filter regeneration system. The method may include injecting fuel and air into the flame chamber, and igniting a spark within the flame chamber in the presence of the fuel, the air, and engine exhaust received by a filter of the filter regeneration system. Additionally, the method may include sensing a change in electrical conductivity indicative of a presence of a flame in the flame chamber, and determining the presence of the flame within the flame chamber based on the change in electrical conductivity.

DETAILED DESCRIPTION

Figure 1:
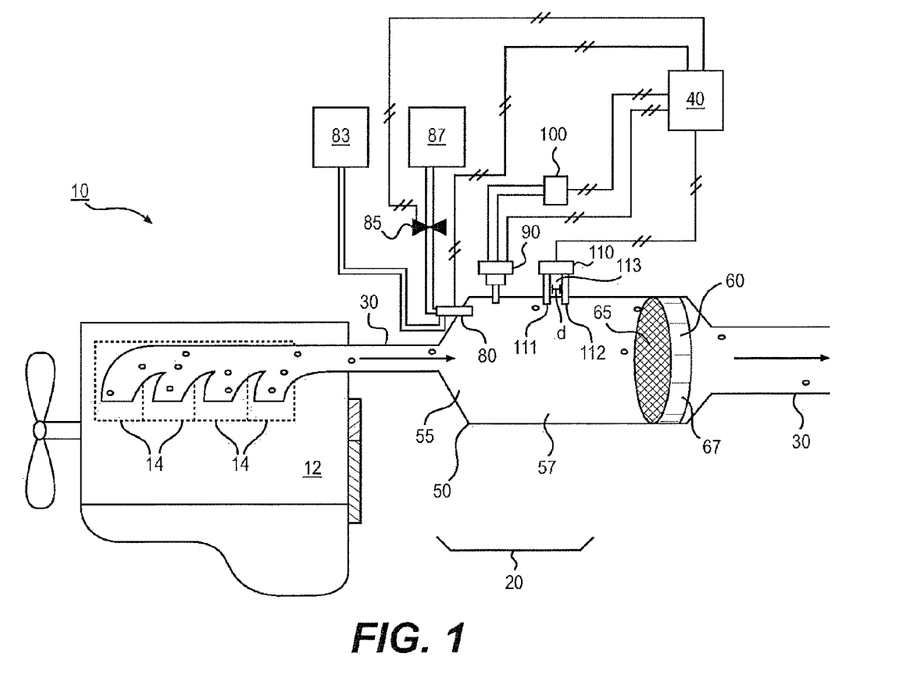
FIG. 1 is a diagrammatic illustration of an exemplary power system associated with a first embodiment of the present disclosure.

FIG. 1 illustrates an exemplary power system 10 having a flame detection system 20 and a filter 60. For the purposes of this disclosure, power system 10 may include an internal combustion engine, for example, a gasoline, diesel, or gaseous fuel-powered engine. Power system 10 may be part of a mobile machine, for example, a long haul truck, a dozer, a motor grader, or a wheel loader. Additionally, in some embodiments, power system 10 may be part of a stationary machine, for example, a furnace, generator set, pumping station, etc.

As shown in FIG. 1, power system 10 may include an engine block 12 that defines at least a plurality of cylinders 14. A plurality of piston assemblies (not shown) may be disposed within cylinders 14 and may form a plurality of combustion chambers. Power system 10 may include any number of combustion chambers and the combustion chambers may be disposed in an "in-line" configuration, a "V" configuration, or in any other conventional configuration.

An exhaust passage 30 may connect engine block 12 with flame detection system 20 and filter 60. Additionally, exhaust passage 30 may connect flame detection system 20 with the atmosphere. Therefore, engine exhaust may pass within exhaust passage 30 from the combustion chambers, through filter 60, and into the atmosphere.

Flame detection system 20 may be part of an aftertreatment system, and may include various components configured to measure electrical conductivity and/or other operational characteristics in the vicinity of filter 60. Additionally, flame detection system 20 may determine the presence of a flame within power system 10 based on such characteristics. The flame may be used for active regeneration of filter 60. Flame detection system 20 may include, among other things, a flame chamber 50, an injector 80, an ignition device 90, and a sensor 110. A controller 40 may regulate and/or control these various components, as discussed in more detail below.

As shown in FIG. 1, flame chamber 50 may include a flame chamber head 55 and a flame chamber body 57. Both flame chamber head 55 and flame chamber body 57 may be in communication with exhaust passage 30. Therefore, engine exhaust may flow from exhaust passage 30 and through flame chamber head 55 and flame chamber body 57. Flame chamber 50 may be of sufficient size for a flame to produce sufficient heat to propagate from flame chamber 50 to filter 60. As shown in FIG. 1, filter 60 may be disposed within the same housing as flame chamber 50. However, in alternative embodiments, flame chamber 50 and filter 60 may include separate respective housings connected by exhaust passage 30.

Injector 80 may be located within flame chamber head 55 and may be configured to supply a fuel/air mixture to flame chamber 50. In some embodiments, injector 80 may be connected to an intake manifold 87, and intake manifold 87 may supply ambient intake air to injector 80. In such embodiments, a valve 85 may regulate the supply of air to injector 80. Additionally, injector 80 may be connected to a fuel supply 83, and fuel supply 83 may supply fuel to injector 80. Fuel supply 83 may be a dedicated fuel supply or a fuel supply associated with the machine to which system 10 is connected. Fuel supply 83 may include a pump (not shown) to selectively direct pressurized fuel to injector 80. Ignition device 90 may be disposed within flame chamber body 57 and may be configured to ignite the fuel/air mixture supplied by injector 80. In some embodiments, ignition device 90 may include a spark plug, glow plug, or any other means capable of igniting the fuel/air mixture. An ignition coil 100 may supply electric current to ignition device 90. A sufficient amount of fuel may be supplied by injector 80 and a sufficient amount of electric current may be supplied by ignition device 90 to ignite a flame that propagates to filter 60.

Sensor 110 may be located proximate ignition device 90. In a first embodiment, sensor 110 may be located between ignition device 90 and filter 60 and within flame chamber 50. For example, in one embodiment, sensor 110 may be disposed through a wall of flame chamber 50 within a pathway of the flame. In one example, sensor 110 may be located within approximately 16 inches of ignition device 90. In alternative examples, sensor 110 may be located greater or less than approximately 16 inches of ignition device 90, depending on the size of flame chamber 50. In a second embodiment, sensor 110 may be located remote from flame chamber 50. Sensor 110, as will be discussed in detail below, may be a plasma sensor configured to sense a characteristic within flame chamber 50, such as, for example, a change in electrical conductivity, and such a change in conductivity may be indicative of a presence of a flame in flame chamber 50.

Controller 40 may be in communication with components of power system 10, including components of flame detection system 20. Controller 40 may be configured to receive information from various sources, and may control the components of power system 10, in an open-loop or closed-loop manner, based on and/or in response to such information. For example, controller 40 may be in communication with sensor 110, ignition device 90, ignition coil 100, injector 80, and/or valve 85. Controller 40 may, in one embodiment, be configured to regulate the amount of fuel/air injected by injector 80 based on the presence or absence of a flame detected by sensor 110. In further embodiments, controller 40 may be configured to determine the presence of a flame based on signals received from injector 80, ignition device 90, ignition coil 100, and/or sensor 110, and may be configured to regulate the amount of fuel/air injected by injector 80 based on the determined presence or absence of a flame.

Filter 60 may include a filter media 65 configured to trap and/or collect particulate matter from engine exhaust. Filter 60 may be any type of filter known in the art, such as, for example, a foam cordierite, sintered metal, or silicon carbide-type filter. Filter media 65 may comprise a substrate made of any material capable of removing particulate matter from engine exhaust. In exemplary embodiments, such a substrate may be coated with, made from, and/or otherwise include catalyst materials including alumina, platinum, rhodium, barium, cerium, alkali metals, alkaline-earth metals, rare-earth metals, or combinations thereof. Filter media 65 may be disposed within a filter housing 67 made of a conductive material, including, for example, stainless steel, steel, and iron.

Figure 2:
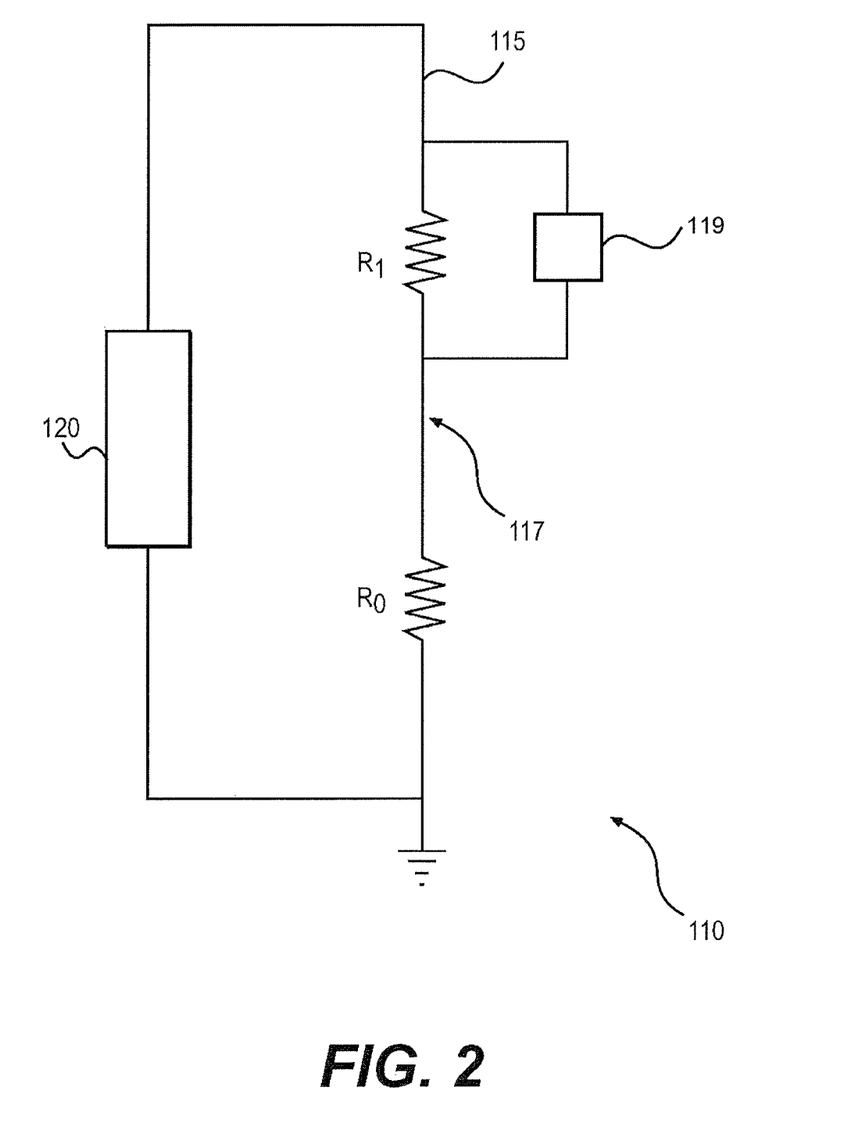
FIG. 2 is a schematic illustration of a circuit associated with the first embodiment.

As shown in FIG. 1, in a first embodiment, sensor 110 may be disposed within flame chamber 50. In the various embodiments of the present disclosure, sensor 110 may comprise any type of sensor circuit known in the art, and may include one or more voltage, resistance, capacitance, inductance, power distribution, and/or like components typically included in such circuits. For example, as shown in the exemplary embodiment of FIG. 2, sensor may comprise a circuit loop 115, having a sensing element 119, a voltage divider 117 including at least one resistor, and a power source 120 (FIG. 2). Sensing element 119 may be connected in parallel to voltage divider 117, and may include, for example, a capacitor or a resistor. Sensing element 119 may include at least two electrodes, for example a pair of electrodes including electrodes 111, 112, positioned upstream of filter 60. Electrodes 111, 112 may include conductive plates or sheets spaced by a gap 113, as shown in FIG. 1. Gap 113 may have a distance d, and may extend from a first electrode 111 to a second electrode 112 opposite the first electrode 111. The conductive plates or sheets may be made from conductive materials including, but not limited to, carbon nanotubes, carbon fibers, stainless steel or non-stainless steel, tantalum, platinum, tungsten, silver, gold, nickel alloys, and/or copper. In an exemplary embodiment, voltage divider 117 may include two resistors $R_1$, $R_o$ in series. An output voltage of voltage divider 117 may increase with the presence of a flame in flame chamber 50. In alternative embodiments, circuit loop 115 may include a wheatstone bridge configuration with four resistors, such that an output voltage of the wheatstone bridge may increase with the presence of a flame in flame chamber 50. Power source 120 may include a voltage source, for example a constant, stable, or regulated voltage source. In other embodiments, power source 120 may include any type of battery known in the art.

Resistors $R_1$, $R_o$ may be disposed within controller 40, and electrodes 111, 112 of sensing element 119 may be disposed within flame chamber 50. It is also contemplated that resistors $R$, $R_o$ may be disposed external to controller 40. Electrodes 111, 112 of sensing element 119 may be arranged in any location within flame chamber 50 between injector 80 and filter 60, such that a flame may pass within gap 113 between electrodes 111, 112. Additionally, air may pass within gap 113 when no flame is present. Electrodes 111, 112 may be disposed within an insulating material, including, for example, materials fabricated from aluminum oxide, aluminum nitride, porcelain, boron nitride, or other insulating elements.

It is understood that the flame may comprise plasma material having conductive properties that may alter the conductivity of sensing element 119. Additionally, sensing element 119 may be configured to impede a flow of electric current in circuit loop 115 in the absence of a flame and to permit the flow of a current in presence of the flame. For example, when no flame is present, air and engine exhaust may be disposed within and/or may pass through gap 113 between electrodes 111, 112 of sensing element 119. It is understood that air is a dielectric, and therefore has a high resistance, compared to the resistance of the plasma flame, that may impede current flow. For example, due to the relatively high resistance associated with gap 113 of sensing element 119, current within circuit loop 115 may not flow through sensing element 119 when no flame is present. When a flame is present within flame chamber 50, however, the flame may flow within gap 113 between electrodes 111, 112, and may decrease the electrical resistance of sensing element 119. As a result, the presence of such a flame may enable and/or otherwise facilitate the flow of electric current within circuit loop 115 through sensing element 119.

In one embodiment, a resistance value associated with resistor $R_1$ may be equal to approximately 10 KOhm, a resistance value associated with resistor $R_o$ may be equal to approximately 1 KOhm, and power source 120 may include a 120 volt voltage source. Such values may produce a signal from circuit loop 115 having reduced noise and such signals may be easily sensed by controller 40. It is contemplated that the above resistance and voltage values are merely exemplary. In additional embodiments, resistors $R_1$, $R_o$ and power source 120 may have respective resistance and voltage values greater than or less than the value listed above. Sensing element 119 may have a resistance equal to the resistance of air when no flame is present (i.e. greater than approximately $10^9$ Ohm), and may have a resistance ranging from approximately 10 KOhm to approximately 100 KOhm when a flame is present. The strength of the flame may vary the resistance of sensing element 119, such that a stronger flame may affect a lower resistance of sensing element 119 than a relatively weaker flame. It is understood that as described herein, the relative strength or weakness of a flame may be quantified and/or otherwise determined based on, for example, the axial length of the flame, the temperature of the flame, the color of the flame, the quantity of plasma material associated with the flame, and/or any other flame strength metric known in the art. For example, a "stronger" flame may be characterized by a longer axial length, a higher temperature, a higher wavelength of emitted light (i.e., closer to the violet end of the visible color spectrum), and/or a greater quantity of plasma material than a relatively "weaker" flame.

Figure 3:
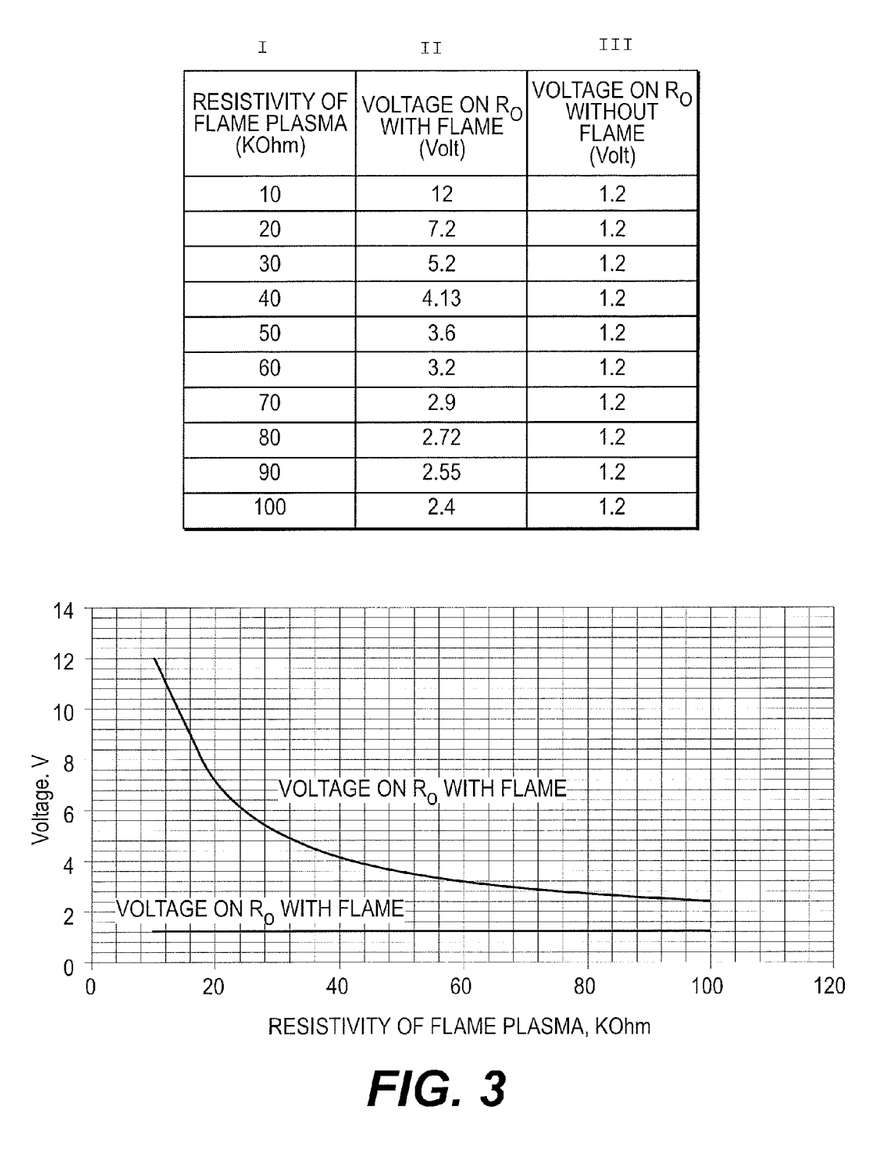
FIG. 3 is a table and graph associated with the first embodiment.

As shown in FIG. 3, the resistance of sensing element 119 may alter the output voltage of voltage divider 117. The voltage across and/or associated with resistor $R_o$ may equal the output voltage of voltage divider 117, and may be indicative of the presence of flame. Column I in FIG. 3 shows the changing resistivity of sensing element 119 due to the strength of a flame within flame chamber 50. A stronger flame may correspond to a lower resistivity of sensing element 119, and may produce a higher voltage across $R_o$. Column II in FIG. 3 shows the voltage across $R_o$ corresponding with the changing resistivity of sensing element 119. Additionally, column III shows a constant voltage across $R_o$ corresponding to the absence of a flame in flame chamber 50. FIG. 3 shows a graph displaying the varying voltage across resistor $R_o$ compared to the constant voltage across resistor $R_o$. It is understood that the resistance and voltage values listed in FIG. 3 are merely exemplary. In additional embodiments, exemplary resistance values associated with resistors $R_1$, $R_o$ may be greater or less than those listed in FIG. 3.

In one example, when no flame is present, $R_o$ may have a constant voltage for example 1.2 volts, as shown in column III of FIG. 3 In this scenario, no current may flow through sensing element 119 and therefore the output voltage of voltage divider 117 may only be dependent on $R_1$ and $R_o$. However, the presence of a flame within flame chamber 50 may decrease the resistance of sensing element 119. As a result, current may flow through $R_1$, $R_o$, and sensing element 119. Additionally, the amount of current through sensing element 119 may vary based on the strength, for example axial length, of the flame. The voltage across $R_o$, may vary from between approximately 12 volts, when a stronger flame is present, to about 2.4 volts when a weaker flame is present, as shown in column II of FIG. 3.

Controller 40 may also include a voltage measurement device (not shown) configured to measure a voltage drop across and/or associated with $R_o$, and controller 40 may be configured to determine the presence of a flame based, at least in part, on such measurements. For example, as shown in FIG. 3, controller 40 may measure a constant voltage across $R_o$ when no flame is present. Additionally, controller 40 may be configured to measure the varying voltage across $R_o$ when a flame is present. The voltage measurement device of controller 40 may determine the presence of a flame based on such voltage measurements. In alternative embodiments, sensor 110 may be configured to measure the voltage drop across and/or associated with $R_o$, and may send the information to controller 40. In still further embodiments, sensor 110 may be configured to determine the presence and/or absence of a flame based on the measured voltage drop across $R_o$, and may be configured to send such flame determination information to controller 40.

Controller 40 may additionally include one or more software and/or hardware components configured to manipulate and/or process a signal from circuit loop 115. For example, such components may be configured to filter the output voltage of voltage divider 117. In some embodiments, controller 40 may include a data acquisition system (not shown) configured to perform digital to analog conversion of the output voltage. The data acquisition system may further store the voltage data until a processor of controller 40 processes the data. It is further contemplated that the one or more software and/or hardware components of controller 40 may be formed as separate components distinct from controller 40.

It is also contemplated that resistors $R_1$, $R_o$ may include capacitors (not shown), and the voltage measurement device of controller 40 may measure the voltage across the capacitors. This voltage may be indicative of the presence of a flame within flame chamber 50.

Figure 4:
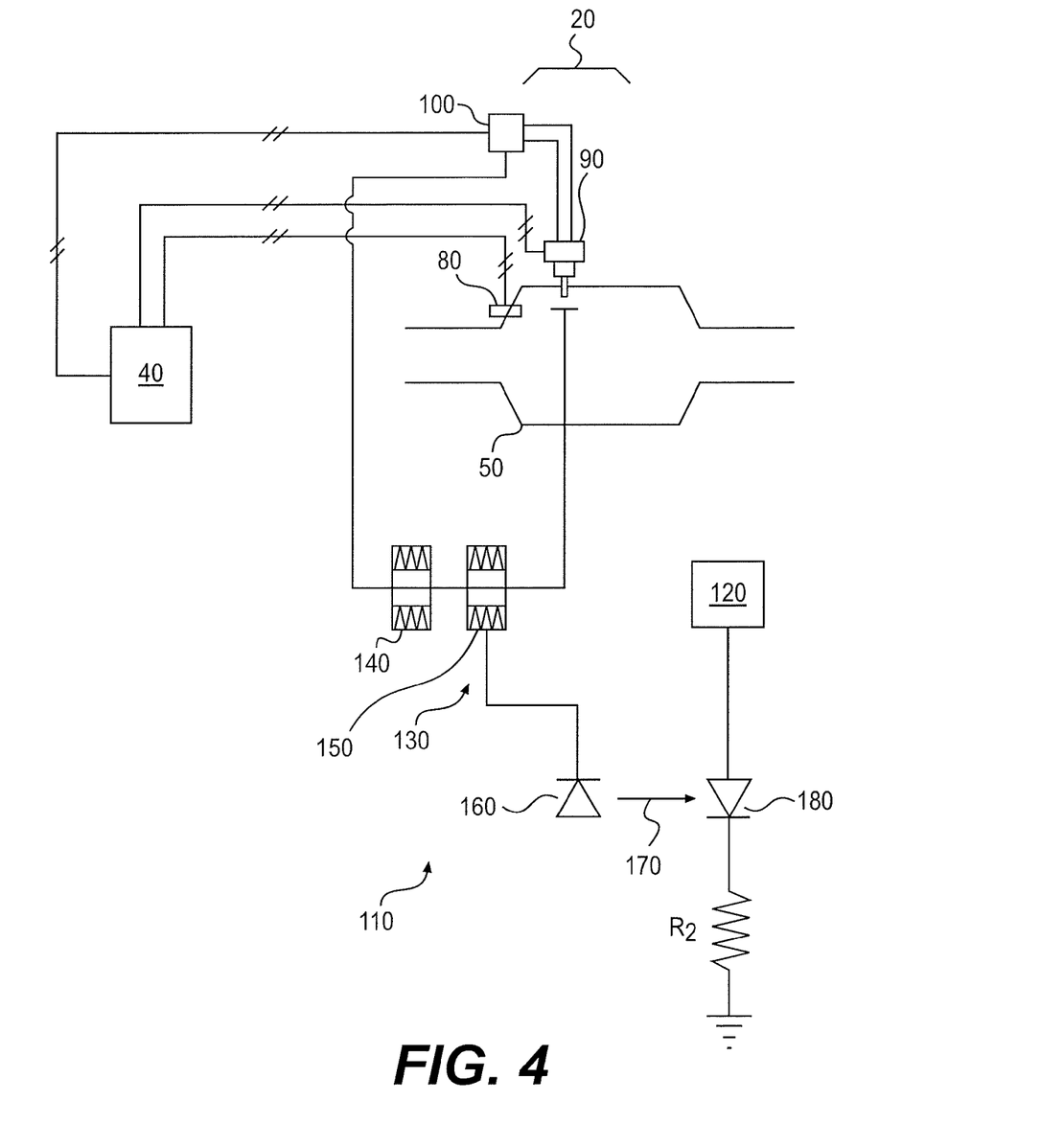
FIG. 4 is a schematic illustration of a circuit associated with a second embodiment of the present disclosure.

As shown in FIG. 4, sensor 110, in a second embodiment, may be disposed external to and remote from flame chamber 50. In this second embodiment, controller 40 may be configured to measure an output voltage of a sensor circuit, circuit loop 130, in response to a flame within flame chamber 50, and to determine an increase in electric current within ignition device 90. An increase in current may be indicative of a presence of a flame within flame chamber 50. Additionally, controller 40 may be configured to determine the amplitude of a pulse signal from light-emitting diode 160 to photo diode 180. Based on the amplitude of the signal, controller 40 may be configured to determine the strength (e.g. axial length) of a flame within flame chamber 50. In such an embodiment, sensor 110 may include current transformers 140, 150, light-emitting diode 160, photo diode 180, and resistor $R_2$ electrically connected within circuit loop 130. Additionally, circuit loop 130 may connect resistor $R_2$ with controller 40, and may connect current transformers 140, 150 with ignition coil 100 and ignition device 90. Circuit loop 130 may also connect to power source 120, wherein power source 120 may include a voltage source, for example a constant, stable, or regulated voltage source. In other embodiments, power source 120 may include any type of battery known in the art.

Ignition coil 100 may send electric current to ignition device 90 and within circuit loop 130. Current transformers 140, 150 may be configured to induce a magnetic field within circuit loop 130 and amplify the electric current produced by ignition coil 100. For example, current transformers 140, 150 may each include primary and secondary coils (not shown) configured to deliver amplified current to light-emitting diode 160. The primary and secondary coils may have a winding ratio between approximately 10:1 and approximately 1000:1, for example between 20:1 and 200:1. However, the ratio may be adjusted for a particular system as needed. Current transformers 140, 150 may include a donut, circular, or C-shaped core.

Light-emitting diode 160 may include one or more semiconductors configured to generate light 170 and direct the generated light 170 to photo diode 180 in response to a flame within flame chamber 50. In exemplary embodiments, such light 170 may comprise a beam of optical and/or thermal radiation that impinges upon photo diode 180. Light 170 may comprise a pulse signal having an amplitude and a duration. The amplitude may vary based on the current within circuit loop 130, such that a relatively larger increase in current may correspond to a relatively larger amplitude, compared to a relatively smaller increase in current. Light-emitting diode 160 may include any configuration known in the art, and may include an LED chip having an active region (not shown), and an encapsulating region (not shown). Light 170 emitted from light-emitting diode 160 may impinge upon photo diode 180 and excite electrons within photo diode 180. As shown in FIG. 4, photo diode 180 may be configured to produce an electric current in response to this excitation, and the current produced by photo diode 180 may flow across resistor $R_2$. Photo diode 180 may include one or more semiconductors formed of silicon.

In the exemplary embodiment shown in FIG. 4, controller 40 may include various components, including a voltage measurement device, as discussed above, configured to measure a voltage drop across and/or associated with resistor $R_2$. Controller 40 may be configured to determine the presence of a flame based, at least in part, on the measurements of the voltage measurement device. The voltage across $R_2$ may be proportional to the current in ignition device 90. Therefore, controller 40 may determine that an increase in voltage across $R_2$ corresponds to an increase in current within ignition device 90. An increase in current within ignition device 90 may indicate that a flame is present within flame chamber 50.

INDUSTRIAL APPLICABILITY

The disclosed flame detection system may provide a faster and more accurate detection of the presence of flame compared with traditional systems. In a first embodiment, flame detection system 20 may include at least injector 80, ignition device 90, and sensor 110. Injector 80 may inject a fuel/air mixture into flame chamber 50. Ignition device 90 may receive electric current from ignition coil 100, and in response, may ignite a spark within flame chamber 50 in the presence of the fuel/air mixture and engine exhaust received by filter 60. The spark may ignite the fuel/air mixture and may form a flame sufficient to propagate within flame chamber 50 and capable of regenerating filter 60. The flame may, for example, increase the temperature of the exhaust passing through filter 60 to at least approximately 300° C., for example, to at least approximately 600° C., to ensure active regeneration of filter 60. Gap 113 may be positioned with flame chamber 50 such that at least a portion of the flame passes through gap 113.

In this first embodiment, sensing element 119 may impede a flow of electric current within circuit loop 115 in the absence of at least a portion of a flame within gap 113, and may permit a flow of electric current in the presence of the portion of the flame within gap 113. Controller 40 may measure the output voltage of voltage divider 117, which may be dependent on sensing element 119, to determine the presence of a flame within flame chamber 50 (FIG. 2). When no flame is present, the resistance of sensing element 119 may be constant and equal to the resistance of the dielectric material between electrodes 111, 112 (i.e. air). In one embodiment, sensing element 119 may have a resistance equal to approximately $10^9$ Ohm. Therefore, controller 40 may measure a constant voltage across $R_o$. In one example, controller 40 may measure a constant voltage of approximately 1.2 V when no flame is present, as shown in column III of FIG. 3.

As explained above, the resistance of sensing element 119 may decrease when a flame is present. In one example, the resistance of sensing element 119 may decrease to a value ranging between approximately 10 KOhm and approximately 100 KOhm (column I of FIG. 3). Therefore, in the presence of a flame, controller 40 may measure an increased voltage across $R_o$. As shown in column II of FIG. 3, the voltage measured across $R_o$ may also be a function of energy dissipated by the plasma flame, such that a stronger flame, having a longer axial length, will cause a larger voltage increase. Controller 40 may detect the propagation of the flame by comparing the voltage increase to the constant voltage detected when no flame is present (e.g. approximately 1.2 V). For example, a voltage of 12 V, as shown in FIG. 3, may correspond to a flame with a longer axial length than a flame associated with a voltage of 2.4 V.

Sensor 110 may allow controller 40 to detect the presence of a flame in a reduced amount of time as compared to thermocouple sensors. For example, controller 40 may measure the voltage of voltage divider 117 and determine the presence of flame within approximately 0.1 milliseconds to approximately 0.01 milliseconds of ignition of the flame by ignition device 90. Traditional thermocouples, on the other hand, may only have a response time as high as 1.5 seconds.

In a second embodiment, flame detection system 20 may include at least injector 80, ignition device 90, and sensor 110. Ignition device 90 may receive electric current from ignition coil 100 and ignite a spark within flame chamber 50 in the presence of the fuel/air mixture and engine exhaust received by filter 60. The spark may ignite the fuel/air mixture and may form a flame sufficient to propagate within flame chamber 50 and capable of regenerating filter 60. The flame may, for example, increase the temperature of the exhaust passing through filter 60 to at least approximately 300° C. to ensure active regeneration of filter 60.

Ignition coil 100 may additionally send current to transformers 140, 150, within circuit loop 130, in response to a flame within flame chamber 50. Transformers 140, 150 may amplify the received current, and allow controller 40 to more easily measure the voltage across resistor $R_2$. The amplified current may flow into light-emitting diode 160 and into photo diode 180. Light-emitting diode 160 may produce light 170 that may impinge upon photo diode 180 and excite electrons within photo diode 180. In response to the excited electrons, photo diode 180 may become conductive and may allow the amplified current received from transformers 140, 150 to flow from photo diode 180 to resistor $R_2$.

Controller 40 may measure the voltage across resistor $R_2$, and may determine the presence of a flame within flame chamber 50 based on the measured voltage. The voltage across resistor $R_2$ may be proportional to the electric current within ignition device 90. An increase in current within ignition device 90 may correspond to a spark within flame chamber 50 igniting the fuel/air mixture. Therefore, an increase in current within ignition device 90 may correspond to a flame within flame chamber 50. Controller 40 may measure the voltage across resistor $R_2$ and may determine that an increase in voltage corresponds to an increase in current within ignition device 90, which corresponds to the presence of a flame within flame chamber 50. In one example, controller 40 may measure an increase in voltage across resistor $R_2$ and determine that a flame is present in flame chamber 50. Alternatively, controller 40 may measure a constant voltage across resistor $R_2$ and determine that no flame is present within flame chamber 50. Controller 80 may also measure the amplitude of a pulse signal from light-emitting diode 160 to photo diode 180, and determine the strength of the flame within flame chamber 50 based on the amplitude. For example, an increase in current from ignition coil 100 may correspond to an increase in amplitude of the pulse signal from light-emitting diode 160. Additionally, a relatively larger increase in current from ignition device 100 may correspond to a relatively stronger flame (e.g. a flame having a relatively long axial length) within flame chamber 50. Therefore, controller 40 may determine the strength of the flame based on the amplitude of the pulse signal. For example, controller 40 may determine that a larger amplitude corresponds to a stronger flame.

The present disclosure provides a faster and more accurate detection of a flame for filter regeneration systems relative to systems using thermocouples. This may result in less unburned fuel inadvertently flowing into a filter and damaging the filter. Such a reduction may increase the life of the filter and create a more efficient engine. The embodiments of the present disclosure may also provide systems that allows for easy and reliable measurements to determine the presence of a flame. Additionally, the embodiments described herein may determine the propagation of the flame using fewer components than traditional thermocouple systems, and as a result, may be less complicated and more robust than the traditional thermocouple systems.

It will be apparent to those skilled in the art that various modifications and variations can be made to the system of the present disclosure. Other embodiments of the system will be apparent to those skilled in the art from consideration of the specification and practice of the method and system disclosed herein. It is intended that the specification and examples be considered as exemplary only, with a true scope of the disclosure being indicated by the following claims and their equivalents.

What is claimed is:

1. A flame detection system, comprising:
   a flame chamber;
   a filter disposed downstream of the flame chamber, the filter including filter media configured to collect matter from an engine exhaust;
   an ignition device disposed in the flame chamber and configured to ignite a flame in the flame chamber to regenerate the filter; and
   a sensor disposed proximate the ignition device,
   wherein the sensor is configured to sense a change in electrical conductivity that is indicative of a presence of the flame in the flame chamber, and
   wherein the sensor includes at least two electrodes connected in parallel to a voltage divider.

2. The flame detection system of claim 1, wherein the sensor is disposed in the flame chamber.

3. The flame detection system of claim 2, wherein an output voltage of the voltage divider increases in response to the presence of the flame in the flame chamber.

4. The flame detection system of claim 3, wherein a resistance of the electrodes decreases in response to the presence of the flame in the flame chamber.

5. The flame detection system of claim 3, further including a controller in communication with the sensor, wherein the controller is configured to determine the output voltage of the voltage divider and to determine the presence of the flame in the flame chamber based on the output voltage.

6. The flame detection system of claim 2, wherein the sensor is disposed within a pathway of the flame.

7. The flame detection system of claim 6, wherein the sensor includes a sensing element comprising a pair of electrodes spaced by a gap, the gap positioned to accept at least a portion of the flame.

8. The flame detection system of claim 7, wherein the sensing element is configured to impede a flow of electric current in a sensor circuit in the absence of the flame in the flame chamber and to permit the flow of electric current in the presence of the flame in the flame chamber.

* * * * *